United States Patent [19]

Grigsby, Jr. et al.

[11] Patent Number: 4,558,072
[45] Date of Patent: Dec. 10, 1985

[54] PROCESS FOR PREPARING ETHYLENE GLYCOL AND LOWER MONOHYDRIC ALCOHOLS FROM SYNGAS USING A NOVEL CATALYST SYSTEM

[75] Inventors: Robert A. Grigsby, Jr., Georgetown; John F. Knifton, Austin, both of Tex.

[73] Assignee: Texaco Inc., White Plains, N.Y.

[21] Appl. No.: 552,631

[22] Filed: Nov. 16, 1983

[51] Int. Cl.[4] ............................................. C07C 27/06
[52] U.S. Cl. ..................................... 518/701; 518/700
[58] Field of Search ................................. 518/700, 701

[56] References Cited

U.S. PATENT DOCUMENTS

| | | | |
|---|---|---|---|
| 4,315,994 | 2/1982 | Knifton | 518/700 |
| 4,362,821 | 12/1982 | Lin | 518/700 |
| 4,396,726 | 8/1983 | Simons | 518/700 |

FOREIGN PATENT DOCUMENTS

| | | | |
|---|---|---|---|
| 33425 | 8/1981 | European Pat. Off. | 518/700 |
| 75937 | 4/1983 | European Pat. Off. | 518/701 |
| 58-29728 | 2/1983 | Japan | 518/700 |

*Primary Examiner*—Howard T. Mars
*Attorney, Agent, or Firm*—Jack H. Park; Kenneth R. Priem; Cynthia L. Kendrick

[57] ABSTRACT

Ethylene glycol along with ethylene glycol derivatives and alcohols are prepared from syngas in improved yields by contacting a mixture of carbon monoxide and hydrogen with a catalyst system comprising a ruthenium-containing compound and a manganese-containing compound, both dispersed in a low melting quaternary phosphonium compound dissolved in a solvent and heating the resulting reaction mixture at a temperature of at least 150° C. and a pressure of at least 30 atm. for sufficient time to produce the desired ethylene glycol and monohydric alcohols, and then recovering the same from the reaction mixture. A rhodium-containing compound may optionally be used with the ruthenium-containing compound.

3 Claims, No Drawings

PROCESS FOR PREPARING ETHYLENE GLYCOL AND LOWER MONOHYDRIC ALCOHOLS FROM SYNGAS USING A NOVEL CATALYST SYSTEM

FIELD OF THE INVENTION

This invention relates to a new process for preparing ethylene glycol along with ethylene glycol derivatives from syngas using a novel catalyst system which allows for improved yields and selectivity to ethylene glycol.

More particularly, the invention provides a new and improved process for preparing ethylene glycol, ethylene glycol monomethyl ether, ethylene glycol monoethyl ether, methanol, and ethanol from syngas in improved yields, said process comprising contacting a mixture of carbon monoxide and hydrogen with a catalyst comprising a ruthenium-containing compound, optionally a rhodium-containing compound, and a manganese-containing compound, all dispersed in a low melting quaternary phosphonium salt dissolved in a solvent and heating the resulting mixture at a temperature of at least 150° C. and a pressure of at least 30 atm. for sufficient time to produce the desired ethylene glycol and derivatives.

BACKGROUND OF THE INVENTION

Ethylene glycol is a chemical which has found wide use in industry. It is used, for example, in the preparation of plasticizers for vinyl polymers and as a component in polyester fibers and antifreeze formulations. In view of its many uses, there is a need to find new and more economical methods for preparing the ethylene glycol.

Proposed methods of making ethylene glycol involve the reaction of carbon monoxide with hydrogen in the presence of variously proposed catalyst systems. In general, the mixture of carbon monoxide and hydrogen, commonly known as synthesis gas, is reacted at elevated temperatures and pressures in the presence of the proposed catalysts. For example, Belgium Pat. No. 793,086 and U.S. Pat. No. 3,940,432, describe the cosynthesis of ethylene glycol and methanol from mixtures of carbon monoxide and hydrogen using a complex rhodium catalyst. U.S. Pat. No. 3,833,634 describes the use of various other metals as catalysts but indicates that only rhodium and cobalt were effective in producing the ethylene glycol. Here the typical yield of ethylene glycol produced was 9.8 parts out of 58 parts.

U.S. Pat. No. 3,989,799 discloses a series of carbonyl mixed metal salt useful as catalyst in the reaction between carbon monoxide and hydrogen to produce oxygenated compounds. There are no selectivities reported for particular products such as ethylene glycol. There is no mention of the use of a quaternary onium salt.

In U.S. Pat. No. 4,013,700, Cawse discloses a process for producing polyhydric alcohols, their ether and ester derivatives in the presence of a quaternary phosphonium cation and a rhodium carbonyl complex. This system produces moderate quantities of ethylene glycol as demonstrated by yields of 4.2 grams and less.

U.S. Pat. No. 4,265,828, Knifton, 1981, discloses a process of making ethylene glycol which comprises the steps of contacting a mixture of CO and H$_2$ with a catalyst system comprising a ruthenium-containing compound dispersed in a low-melting quaternary phosphonium or ammonium base or salt and heating said resultant reaction mixture under a pressure of 500 psi or greater at a temperature of at least 150° C. for a sufficient time to provide said ethylene glycol. The highest yield of ethylene glycol obtained by this process was 17.6 weight percent.

In U.S. Pat. No. 4,315,994 by Knifton, alkylene glycols and their ethers are produced by contacting a mixture of carbon monoxide with a bimetallic catalyst system comprising ruthenium(III) acetylacetonate and rhodium(III) acetylacetonate dispersed in a low melting quaternary onium base or salt at a pressure of at least 150° C. The highest reported selectivity for ethylene glycol was 18.5 weight percent.

Many of these processes are limited by the nature and activity of the catalyst systems. Most catalysts provide only moderate selectivity to desired glycol, limited solubility and/or are expensive to prepare.

It would be a significant advance in the art to provide an improved method for preparing ethylene glycol and monohydric alcohols which provides ethylene glycol with greater yields and selectivity.

SUMMARY OF THE INVENTION

It has now been discovered that these and other desirable results may be accomplished by the process of the invention comprising contacting a mixture of carbon monoxide and hydrogen with a catalyst comprising a ruthenium-containing compound and a manganese containing compound both dispersed in a low melting quaternary phosphonium salt dissolved in a solvent and heating the resulting mixture at a temperature of at least 150° C. and a pressure of at least 30 atm. for sufficient time to produce the desired ethylene glycol and glycol derivatives including ethylene glycol monomethyl ether, ethylene glycol monethyl ether, methanol, and ethanol. A rhodium-containing compound can optionally be used with the ruthenium-containing compound. It was surprising to find that by the use of this new catalyst system one can obtain greater yield and selectivity in the formation of the ethylene glycol and can obtain the said glycol in higher yields than obtainable heretofore in related synthesis processes from syngas.

The process of the invention as far as the formation of the desired ethylene glycol is concerned may be represented by the following equation:

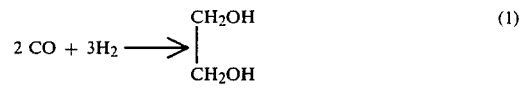
(1)

Typical yields of ethylene glycol based on total liquid products range from 10 to about 40 wt %.

DETAILED DESCRIPTION OF THE INVENTION

In the operation of the process of the invention, ethylene glycol and glycol derivatives of the group including ethylene glycol monomethyl ether, ethylene glycol monethyl ether, plus methanol and ethanol are prepared concurrently from a synthesis gas mixture of carbon monoxide and hydrogen by a process comprising the following steps:

(a) contacting said mixture of carbon monoxide and hydrogen with a catalyst comprising a ruthenium-containing compound optionally with a rhodium-containing compound and a manganese-containing compound, both dispersed in a low melting quaternary phosphonium salt dissolved in a solvent, (b) heating said mixture to a temperature of at least 150° C. and a pressure of at least 30 atm. with sufficient carbon monoxide and hydrogen to satisfy the above-noted stoichiometry of the desired ethylene glycol synthesis, until substantial formation of the desired ethylene glycol has been achieved, and, (c) preferably isolating the said ethylene glycol and aforementioned ethylene glycol derivatives contained therein.

In order to present the inventive concept of the present invention in the greatest possible detail, the following supplementary disclosure is submitted. The process of the invention is practiced as follows:

As noted, the new catalyst system used in the process of the invention contains a ruthenium-containing compound, optionally with a rhodium-containing compound, and a manganese-containing compound. The ruthenium-containing compound to be used may be chosen from a wide variety of organic and inorganic compounds, complexes, etc. It is only necessary that the catalyst component actually employed contain the ruthenium in any of its ionic states.

The ruthenium-containing compound employed may take many different forms. For example, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium nitrate, or as the salt of a suitable organic carboxylic acid, such as, for example, ruthenium(III) acetate, ruthenium naphthenate, ruthenium valerate and ruthenium complexes such as ruthenium(III) acetylacetonate. The ruthenium may also be added to the reaction mixture as a carbonyl or hydrocarbonyl compound or derivative thereof. Suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonyl-ruthenium(II) chloride dimer, $[Ru(CO)_3Cl_2]_2$.

Preferred ruthenium-containing compounds include oxides of ruthenium, ruthenium salts of organic carboxylic acids and ruthenium carbonyl or hydrocarbonyl derivatives. Particularly preferred are the following: ruthenium(IV) dioxide hydrate, ruthenium(VIII) tetraoxide, anhydrous ruthenium(IV) oxide, ruthenium acetate, ruthenium(III) acetylacetonate, ruthenium propionate and triruthenium dodecacarbonyl.

In one embodiment of the invention a rhodium-containing compound is used along with the ruthenium-containing compound and manganese-containing compound in a catalyst system. The rhodium-containing compound used may be selected from a variety of organic and inorganic compounds, complexes, etc. It is only necessary that the catalyst component actually employed contain the rhodium in any of its ionic states.

The rhodium-containing compound employed may take many different forms. For example the rhodium may be added to the reaction mixture in an oxide form, as in the case of for example, rhodium(III) oxide. Alternatively it may be added as the salt of a suitable organic carboxylic acid, as in the case of rhodium(II) acetate, rhodium(II) propionate, rhodium(III) naphthenate. Other examples of suitable rhodium-containing compounds include carbonyls and hydrocarbonyls such as tetrarhodium dodecacarbonyl and hexarhodium hexadecacarbonyl, as well as rhodium(III) acetylacetonate, chlorocarbonyl-bis(triphenylphosphine)rhodium(I), chlorodicarbonylrhodium(I) dimer, dicarbonyl-(acetylacetonate)rhodium(I), tris(2,2-bipyridyl)rhodium(III) chloride and sodium hexachlororhodate(III) hydrate. The preferred rhodium-containing precursor is dicarbonyl(acetylacetonate)rhodium(I).

The manganese compounds to be used in the catalyst composition comprise those compounds which have one manganese atom attached to carbon, and preferably those organometallic compounds having one manganese atom attached to three separate carbonyl groups and to an unsaturated hydrocarbon radical. Examples of these include, among others, allyl manganese tricarbonyl, cyclohexadienyl manganese tricarbonyl, butadienyl manganese tricarbonyl, cyclohexenyl manganese tricarbonyl, methylcyclopentenyl manganese tricarbonyl, and the like. Preferred manganese compounds include those of the formula:

$$Y\ Mn(CO)_3$$

wherein Y is an unsaturated aliphatic or cycloaliphatic hydrocarbon radical containing 2 to 16 carbon atoms, such as, for example, the allylic radical, the cyclopentadienyl, cyclohexadienyl, and alkyl or aryl substituted derivatives, such as methylcyclopentadienyl, phenylcyclopentadienyl, butylcyclohexadienyl radicals and the like.

Particularly preferred manganese compounds to be utilized include allyl manganese tricarbonyl, cyclopentadienyl manganese tricarbonyl and methylcyclopentadienyl manganese tricarbonyl.

The ruthenium-containing compound and optionally rhodium-containing compound and the manganese-containing compound are preferably first dispersed in a low melting quaternary phosphonium base or salt. The quaternary phosphonium base or salt selected must be relatively low melting, i.e. have a melting point below the temperature of the reaction. Usually quaternary phosphonium compounds employed have a melting point less than about 180° C. and preferably a melting point less than 150° C.

Suitable quaternary phosphonium salts have the formula:

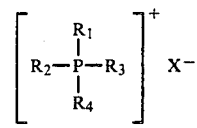

$$\left[\begin{array}{c} R_1 \\ | \\ R_2-P-R_3 \\ | \\ R_4 \end{array}\right]^+ X^-$$

wherein $R_1$, $R_2$, $R_3$ and $R_4$ are organic radicals, particularly aliphatic hydrocarbon radicals, bonded to the phosphorous atom, and X is an anionic species, preferably chlorine or bromide. The preferred organic radicals useful in this instance include those alkyl radicals having 1 to 20 carbon atoms in a branched or linear chain, such as methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, benzoates, butyrates, and the like, are also satisfactory in this instance.

Illustrative examples of suitable quaternary phosphonium salts include tetrabutylphosphonium bromide, tetraheptylphosphonium bromide, tetrabutylphosphonium acetate, tetrabutylphosphonium benzoate, tetrabutylphosphonium butyrate, octylphosphonium acetate, tetrahexylphosphonium acetate and tetraoctylphosphonium bromide.

The preferred quaternary salts are generally the tetralkylphosphonium salts containing alkyl groups having 1 to 20 carbon atoms, such as methyl, ethyl, butyl, amyl, hexyl and isobutyl. Tetrabutylphosphonium bromides are the most preferred.

In the process of this invention the ruthenium-containing compound, rhodium-containing compound, and manganese-containing compound are dispersed in the quaternary phosphonium salt. All these components of the catalyst system are then dissolved in a solvent which is used in the process of this invention and appears to be a significant factor in increasing yields of ethylene glycol. Suitable solvents include the following classes of compounds: alcohols, ethers, esters, hydrocarbons, aromatics, sulfolane, glyme and nitrogen-containing compounds. Examples include, but are not limited to methanol, ethanol, octanol, tetrahydrofuran, methyl phenyl ether, hexane, 1,2 dimethoxyethane decane, benzene, toluene, naphthalene, tetraethylene glycol, pyridine, N,N,N'N'-tetramethylethylene diamine and 1,10 phenanthroline.

Nitrogen-containing compounds work very well as solvents. Nitrogen-containing compounds which can be used in the process of this invention include, for example, N-methylmorpholine, N-(2-hydroxyethyl)-2 pyrrolidone, N-isopropyl-2-pyrrolidine, N-(N,N-dimethylaminopropyl)-2-pyrrolidone, N-cyclohexyl-2-pyrrolidone, N-cocoalkyl-2-pyrrolidone, N-tallowalkyl-2-pyrrolidone, N-methyl-2-pyrrolidone and cyclohexyl-2-pyrrolidone.

Nitrogen-containing compounds which are preferred in the process of this invention include N-alkyl-2-pyrrolidone solvents, such as N-(cyclohexyl)-2-pyrrolidone, N-(isopropyl)-2-pyrrolidone and N-methyl-2-pyrrolidone.

The quantity of ruthenium-containing compound, rhodium-containing compound, when used, and manganese-containing compound to be used in the process of the invention may vary over a wide range. The process is conducted in the presence of a catalytically effective quantity of the active ruthenium-containing compound, rhodium-containing compound, where used, and manganese-containing compound which gives the desired product in a reasonable yield. The reaction proceeds when employing as little as about $1 \times 10^{-6}$ weight percent, or even lesser amounts of the ruthenium-containing compound or $1 \times 10^{-6}$ weight percent ruthenium-containing compound and rhodium-containing compound combined together with as little as about $1 \times 10^{-6}$ weight percent of the manganese compound, or even lesser amounts, based on the total weight of the reaction mixture. The upper concentration is dictated by a variety of factors including catalyst cost, partial pressures of carbon monoxide and hydrogen, operating temperature, etc. A ruthenium-containing compound concentration of from about $1 \times 10^{-5}$ to about 20 weight percent or a ruthenium-containing compound with a rhodium-containing compound concentration of from about $1 \times 10^{-5}$ to about 10 in conjunction with a manganese-containing compound concentration of from about $1 \times 10^{-5}$ to about 10 percent, based on the total weight of the reaction mixture is generally desirable in the practice of this invention. The preferred ruthenium to manganese atomic ratios are from 10:1 to 1:10. The preferred ruthenium to rhodium to manganese atomic ratios are from 10:0:1 to 10:100:100.

Particularly superior results are obtained when the above-noted five components of the catalyst system are combined as follows on a molar basis: ruthenium-containing compound 0.1 to 4 moles, rhodium-containing compound, if used, 0.1 to 4 moles; manganese-containing compound 0.1 to 4 moles, quaternary phosphonium base or salt 10 to 60 moles and solvent 0.1 to 60 moles.

The temperature range which can be employed in the process of the invention may vary over a considerable range depending upon experimental factors, including the choice of catalyst, pressure and other variables. A preferred range of operability is from about 150° C. to about 350° C. when superatmospheric pressures of syngas are employed. A narrower range of about 150° C. to 275° C. represents a particularly preferred temperature range.

The pressure employed may also vary over a considerable range, but in most cases is from at least about 30 atm. to 1700 atm. A preferred operating range varies from about 70 atm. to about 700 atm., although pressures above 700 atm. also provide useful yields of the desired product. The pressures referred to herein represent the total pressure generated by all the reactants, although they are substantially due to the carbon monoxide and hydrogen fractions.

The relative amounts of carbon monoxide and hydrogen which can be initially present in the syngas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon, and the like, or they may include gases that may, or may not, undergo reaction under carbon monoxide hydrogenation conditions, such as carbon dioxide, hydrocarbons, such as methane, ethane, propane, and the like, ethers, such as dimethyl ether, methylethyl ether and diethyl ether, alkanols, such as methanol, and the like.

In all these synthesis in order to achieve a high degree of selectivity the amount of carbon monoxide and hydrogen present in the reaction mixture should be sufficient to at least satisfy the stoichiometry of the desired formation of ethylene glycol as shown in equation (1) above. Excess carbon monoxide and/or hydrogen over the stoichiometric amount may be present, if desired.

The desired product of the reaction, ethylene glycol, will be formed in significant quantities generally varying from about 10 wt % to about 40 wt %. Also formed will be significant amounts of the lower monohydric alcohols, such as methanol and ethanol. Other derivatives such as acetic acid and ethylene glycol ethers, may also be formed in minor amounts. The ethylene glycol, monohydric alcohols and other by-products can be recovered from the reaction mixture by conventional means, e.g. fractional distillation in vacuo.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired ethylene glycol product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), gas chromatography/infrared spectroscopy (CG/IR), nuclear magnetic resonance (nmr) and elemental analyses, or a combination of these techniques. Analyses have, for the most part, been by parts by weight; all temperatures are in degrees centigrade and all pressures in atmospheres.

To illustrate the process of the invention, the following examples are given. It is to be understood, however, that the examples are given in the way of illustration and are not to be regarded as limiting the invention in any way.

Examples I–III demonstrate this invention using a ruthenium-containing compound, without a rhodium-containing compound, but using a manganese-containing compound, a quaternary phosphonium salt and a solvent. Example IV will, for comparison, demonstrate the same process without the use of a solvent.

EXAMPLE I

In Example I a mixture of triruthenium dodecacarbonyl (0.852 g, 1.3 mmole), methylcyclopentadienylmanganese tricarbonyl (0.218 g, 10 mmoles) and tetrabutylphosphonium bromide (10.0 g, 29.4 mmoles) was diluted with 5.0 g N-cyclohexyl-2-pyrrolidone and then transferred in a glass-liner under $N_2$ purge to a 550-ml capacity pressure reactor equipped with heating and means of agitation. The reactor was sealed, flushed with $H_2/CO$ (1:1) and pressured to 204 atm. with $H_2/CO$ (1:1). The reaction mixture was heated to 220° C. with rocking, the pressure raised to 361 atm. with $H_2/CO$ (1:1) addition from the large surge tank and pressure was maintained at 361 atm., by incremental additions from the surge tank. The reactor was held at temperature for 5 hours.

On cooling, the excess gas was sampled and vented, the dark-red liquid product (24.9 g) was recovered and analyzed.

Typical data for the distillate product on a solvent-free basis are as follows:
  39.0% methanol
  19.9% ethanol
  4.1% ethylene glycol monomethyl ether
  1.8 ethylene glycol monoethyl ether
  17.3% ethylene glycol
Analysis of typical gas samples showed the presence of:
  45.5% hydrogen
  5.1% carbon dioxide
  0.0% methane
  48.1% carbon monoxide The calculated yield of ethylene glycol for the example is 25 mmole. The calculated yield of ethylene glycol products for this example is 31 mmole.

The weight percent of ethylene glycol products in the liquid product is 23.3%.

EXAMPLE II

A mixture of triruthenium dodecacarbonyl (0.852 g, 1.3 mmole), methylcyclopentadienylmanganese tricarbonyl (0.218 g, 1.0 mmoles) and tetrabutylphosphonium bromide (10.0 g, 29.4 mmoles) was diluted with 10.0 grams N-cyclohexyl-2-pyrrolidone and was transferred in a glass-liner under $N_2$ purge to a 550-ml capacity pressure reactor equipped with heating and means of agitation. The reactor was sealed, flushed with $H_2/CO$ (1:1) and pressured to 204 atm. with $H_2/CO$ (1:1). The reaction mixture was heated to 220° C. with rocking, the pressure raised to 361 atm. with $H_2/CO$ (1:1) addition from the large surge tank and pressure was maintained at 361 atm. by incremental addition from the surge tank. The reactor was held at temperature for 5 hours.

On cooling the excess gas was sampled and vented, the dark-red liquid product (30.0 g) was recovered and analyzed.

Typical data for the distillate product on a solvent-free basis were as follows:
  41.3% methanol
  18.5% ethanol
  3.8% ethylene glycol monomethyl ether
  1.6% ethylene glycol monoethyl ether
  17.8% ethylene glycol
Analysis of typical gas samples showed the presence of:
  40.6% hydrogen
  8.1% carbon dioxide
  3.2% methane
  46.0% carbon monoxide The calculated yield of ethylene glycol for the example was 24 mmole. The calculated yield of ethylene glycol products for this example was 29 mmole.

The weight percent of ethylene glycol products in the product was 23.2%.

EXAMPLE III

A mixture of triruthenium dodecacarbonyl (0.852 g, 1.3 mmole), methylcyclopentadienylmanganese tricarbonyl (0.218 g, 1.0 mmoles) and tetrabutylphosphonium bromide (10.0 g, 29.4 mmoles) was diluted with 15.0 grams of N-cyclohexyl-2-pyrrolidone and transferred in a glass-liner under $N_2$ purge to a 550-ml capacity pressure reactor equipped with heating and means of agitation. The reactor was sealed, flushed with $H_2/CO$ (1:1) and pressured to 204 atm. with $H_2/CO$ (1:1). The reaction mixture was heated to 220° with rocking, the pressure raised to 361 atm. with $H_2/CO$ (1:1) addition from the large surge tank and the pressure was maintained at 361 atm. by incremental additions from the surge tank. The reactor was held at temperature for 5 hours.

On cooling, the excess gas was sampled and vented, the dark-red liquid product (35.0 g) was recovered and analyzed.

Typical data for the distillate product on a solvent-free basis were as follows:
  16.9% ethanol
  44.2% methanol
  2.9% ethylene glycol monomethyl ether
  1.0% ethylene glycol monoethyl ether
  18.9% ethylene glycol
Analysis of typical gas samples showed the presence of:
  39.6% hydrogen
  7.6% carbon dioxide
  3.1% methane
  46.7% carbon monoxide The calculated yield of ethylene glycol for the example was 25 mmole. The calculated yield of ethylene glycol products for this example is 29 mmole. The weight percent of ethylene glycol products in the product was 22.9%.

COMPARATIVE EXAMPLE IV

In this example, where no solvent was used, a mixture of triruthenium dodecacarbonyl (0.852 g, 1.3 mmole), methylcyclopentadienylmanganese tricarbonyl (0.218 g, 10 mmoles) and tetrabutylphosphonium bromide (10.0 g, 29.4 mmoles) was transferred in a glass-liner under $N_2$ purge to a 550-ml capacity pressure reactor equipped with heating and means of agitation. The reactor was sealed, flushed with $H_2/CO$ (1:1) and pressured to 204 atm. with $H_2CO$ (1:1). The reaction mixture was heated to 220° C. with rocking, the pressure raised to 361 atm. with $H_2/CO$ (1:1) addition from the large surge tank and the pressure was maintained at 361 atm. by incremental additions from the surge tank. The reactor was held at temperature for 5 hours.

On cooling, the excess gas was sampled and vented, the dark-red liquid product (20.3 g) is recovered and analyzed.

Typical data for the distillate product were as follows:
- 38.4% methanol
- 24.7% ethanol
- 4.7% ethylene glycol monomethyl ether
- 2.4% ethylene glycol monoethyl ether
- 10.8% ethylene glycol Analysis of typical gas samples showed the presence of:
- 40.8% hydrogen
- 10.4% carbon dioxide
- 3.6% methane
- 43.3% carbon monoxide The calculated yield of ethylene glycol for the example was 14 mmole. The calculated yield of ethylene glycol products for this example were 22 mmole. The weight percent of ethylene glycol products in the product was 17.9%.

Examples V–VIII along with Example I above illustrate the effect that pressure has on the synthesis of ethylene glycol. It is noted that increases in pressure appear to contribute to improved yields of ethylene glycol.

EXAMPLE V

A mixture of triruthenium dodecacarbonyl (0.852 g, 1.3 mmole), and methylcyclopentadienylmanganese tricarbonyl (0.218 g, 1.0 mmoles) and tetrabutylphosphonium bromide (10.0 g, 29.4 mmoles) was diluted with 5.0 grams N-cyclohexyl-2-pyrrolidone and then transfered in a glass-liner under $N_2$ purge to a 550-ml capacity pressure reactor equipped with heating and means of agitation. The reactor was sealed, flushed with $H_2CO$ (1:1) and pressured to 102 atm. with $H_2/CO$ (1:1). The reaction mixture was heated to 220° with rocking, the pressure raised to 238 atm. with $H_2/CO$ (1:1) addition from the large surge tank and the pressure was maintained at 238 atm. by incremental additions from the surge tank. The reactor was held at temperature fqr 5 hours.

On cooling, the excess gas is sampled and vented, the dark-red liquid product (20.4 g) is recovered and analyzed.

Typical data for the distillate product on a solvent-free basis were as follows:
- 41.5% methanol
- 24.7% ethanol
- 3.1% ethylene glycol monomethyl ether
- 1.5% ethylene glycol monoethyl ether
- 12.7% ethylene glycol Analysis of typical gas samples showed the presence of:
- 41.1% hydrogen
- 7.1% carbon dioxide
- 3.1% methane
- 47.2% carbon monoxide The calculated of ethylene glycol for example was 8 mmole. The calculated yield of ethylene glycol products for this example was 10 mmole.

The weight percent of ethylene glycol products in the product was 17.2%.

EXAMPLE VI

A mixture of triruthenium dodecacarbonyl (0.852 g, 1.3 mmole), methylcyclopentadienylmanganese tricarbonyl (0.218 g, 1.0 mmoles) and tetrabutylphosphonium bromide (10.0 g, 29.4 mmoles) was diluted with 5.0 grams N-cyclohexyl-2-pyrrolidone and was transferred in a glass-liner under $N_2$ purge to a 550-ml capacity pressure reactor equipped with heating and means of agitation. The reactor was sealed, flushed with $H_2/CO$ (1:2) and pressured to 136 atm. with $H_2/CO$ (1:1). The reaction mixture was heated to 220° with rocking, the pressure raised to 306 atm. with $H_2/CO$ (1:1) addition from the large surge tank and is maintained at 306 atm. by incremental additions from the surge tank. The reactor was held at temperature for 5 hours.

On cooling, the excess gas was sampled and vented, the dark-red liquid product (22.1 g) was recovered and analyzed.

Typical data for the distillate product on a solvent-free basis were as follows:
- 39.5% methanol
- 22.4% ethanol
- 4.0% ethylene glycol monomethyl ether
- 1.8% ethylene glycol monoethyl ether
- 15.7% ethylene glycol Analysis of typical gas samples showed the presence of:
- 42.6% hydrogen
- 5.1% carbon dioxide
- 1.7% methane
- 48.1% carbon monoxide The calculated yield of ethylene glycol for the example was 15 mmole. The calculated yield of ethylene glycol products for this example was 19 mmole. The weight percent of ethylene glycol products in the product was 21.4%.

EXAMPLE VII

A mixture of triruthenium dodecacarbonyl (0.852 g, 1.3 mmole), methylcyclopentadienylmanganese tricarbonyl (0.218 g, 1.0 mmoles) and tetrabutylphosphonium bromide (10.0 g, 29.4 mmoles) was diluted with 5.0 grams N-cyclohexyl-2-pyrrolidone and was transferred in a glass-liner under $N_2$ purge to a 550-ml capacity pressure reactor equipped with heating and means of agitation. The reactor is sealed, flushed with $H_2/CO$ (1:1) and pressured to 204 atm. with $H_2/CO$ (1:1). The reaction mixture was heated to 220° C. with rocking, the pressure raised to 429 atm. with $H_2/CO$ (1:1) addition from the large surge tank and was maintained at 429 atm. by incremental additions from the surge tank. The reactor was held at temperature for 5 hours.

On cooling, the excess gas is sampled and vented, the dark-red liquid product (28.1 g) is recovered and analyzed.

Typical data for the distillate product on a solvent-free basis-free was as follows:
  39.6% methanol
  20.9% ethanol
  4.9% ethylene glycol monomethyl ether
  2.0% ethylene glycol monoethyl ether
  14.8% ethylene glycol
Analysis of typical gas samples showed the presence of:
  33.5 hydrogen
  15.5% carbon dioxide
  6.1% methane
  43.2% carbon monoxide
The calculated yield of ethylene glycol for the example was 27 mmole. The calculated yield of ethylene glycol products for this example was 36 mmole. The weight percent of ethylene glycol products in the product was 21.5%.

EXAMPLE VIII

A mixture of triruthenium dodecacarbonyl (0.852 g, 1.3 mmole), and methylcyclopentadienylmanganese tricarbonyl (0.218 g, 1.0 mmoles) and tetrabutylphosphonium bromide (10.0 g, 29.4 mmoles) was diluted with 5.0 grams N-cyclohexyl-2-pyrrolidone and was transferred in a glass-liner under $N_2$ purge to a 550-ml capacity pressure reactor equipped with heating and means of agitation. The reactor was sealed, flushed with $H_2/CO$ (1:1) and pressured to 272 atm. with $H_2/CO$ (1:1). The reaction mixture was heated to 220° with rocking, the pressure raised to 476 atm. with $H_2/CO$ (1:1) addition from the large surge tank and is maintained at 476 atm. by incremental additions from the surge tank. The reactor was held at temperature for 5 hours.

On cooling, the excess gas is sampled and vented, the dark-red liquid product (30.4 g) was recovered and analyzed.

Typical data for the distillate product on a solevent-free basis were as follows:
  38.0% methanol
  17.1% ethanol
  4.7% ethylene glycol monomethyl ether
  1.9% ethylene glycol monoethyl ether
  16.0% ethylene glycol
Analysis of typical gas samples showed the presence of:
  37.8% hydrogen
  10.9% carbon dioxide
  3.0% methane
  46.6% carbon monoxide
The calculated yield of ethylene glycol for the example was 34 mmole. The calculated yield of ethylene glycol products for this example was 45 mmole. The weight percent of ethylene glycol products in the product was 22.6%.

Example IX demonstrates the use of a catalyst containing a ruthenium-containing compound and a rhodium-containing compound in a quaternary phosphonium salt, without use of a manganese compound and solvent.

COMPARATIVE EXAMPLE IX

In Example IX a mixture of triruthenium dodecacarbonyl (0.213 g, 0.33 mmole), dicarbonyl(acetylacetonate) rhodium (I) (0.258 g, 1.0 mmole) and tetrabutylphosphonium bromide (5.0 g, 14.7 mmole) was transferred in a glass-liner under nitrogen purge to a 550-ml capacity pressure reactor flushed with $H_2/CO$ (1:1) and pressured to 204 atm. $H_2/CO$ (1:1). The reaction mixture was heated to 220° C. with rocking. The pressure raised to 361 atm. with $H_2/CO$ (1:1) addition from the large surge tank and was maintained at 361 atm. by incremental additions from the surge tank. The reactor was held at temperature for 5 hours.

On cooling, the excess gas was sampled and vented. The dark-red liquid product (9.9 g) was recovered and analyzed.

Typical data for the distillate product on a solvent-free basis were as follows:
  30.7% methanol
  11.2% ethanol
  3.5% ethylene glycol monomethyl ether
  1.1% ethylene glycol monoethyl ether
  31.8% ethylene glycol
Analysis of typical gas samples showed the presence of:
  48.3% hydrogen
  2.4% carbon dioxide
  0.3% methane
  47.9% carbon monoxide
The liquid yield increase is 4.4 g or 81.0%. The calculated yield of ethylene glycol was 23 mmoles. The calculated number of mmoles of ethylene glycol product was 25 mmoles.

EXAMPLE X

In Example X the process of Example IX was used, however, a solvent was added to the catalyst system.

A mixture of triruthenium dodecacarbonyl (0.213 g, 0.33 mmole) dicarbonyl(acetylacetonate)rhodium(I) (0.258 g, 1.0 mmole) and tetrabutylphosphonium bromide (5.0 g, 14.7 mmole) was dissolved in 5.0 g of 1-cyclohexyl-2-pyrrolidone and was transferred in a glass-liner under $N_2$ purge to a 550-ml capacity pressure reactor equipped with heating and means of agitation. The reactor was sealed, flushed with $H_2/CO$ (1:1) and pressured to 204 atm. psig with $H_2/CO$ (1:1). The reaction mixture was heated to 220° with rocking. The pressure raised to 361 atm. with $H_2/CO$ (1:1) addition from the large surge tank and was maintained at 361 atm. by incremental additions from the surge tank. The reactor was held at temperature for 5 hours.

On cooling, the excess gas was vented, the dark-red liquid product (14.26) is recovered and analyzed.

Typical data for the distillate product on a solvent-free basis are as follows:
  34.6% methanol
  8.9% ethanol
  1.7% ethylene glycol monomethyl ether
  0.3% ethylene glycol monoethyl ether
  37.4% ethylene glycol
Analysis of typical gas samples showed the presence of:
  48.1% hydrogen
  2.1% carbon dioxide
  0.2% methane
  48.3% carbon monoxide
The liquid yield increase was 3.7 g or 68.2% (solvent-free basis). The calculated yield of ethylene glycol was 23 mmoles. The calculated number of mmoles of ethylene glycol products was 23 mmoles.

EXAMPLE XI

The procedure used in Example XI was the same as that used in Examples IX except that a manganese compound was included. Here a mixture of triruthenium dodecacarbonyl (0.213 g, 0.33 mmole), dicarbonyl(acetylacetonate) rhodium (I) (0.258 g, 1.0 mmole), tetrabutylphosphonium bromide (5.0 g, 14.7 mmole) and methyl cyclopentadienylmanganese tricarbonyl (0.055 g, 0.25 mmole) was transferred to a glass-liner under $N_2$ purge to a 550 ml capacity pressure reactor equipped with heating and means of agitation. The reactor was sealed, flushed with $H_2/CO$ (1:1) and pressured to 204 atm. psig with $H_2/CO$ (1:1). The reaction mixture was heated to 220° C. with rocking, the pressure raised to 361 atm. with $H_2/CO$ (1:1) addition from the large surge tank and was maintained at 361 atm. incremental additions from the surge tank. The reactor was held at temperature for 5 hours.

On cooling, the excess gas was vented, the dark-red liquid product (10.4 g) was recovered and analyzed.

Typical data for the distillated product on a solvent-free basis were as follows:
31.4% methanol
12.1% ethanol
3.6% ethylene glycol monomethyl ether
1.1% ethylene glycol monoethyl ether
29.2% ethylene glycol
Analysis of typical gas samples show the presence of:
48.8% hydrogen
2.1% carbon dioxide
0.3% methane
49.0% carbon monoxide The liquid yield increase was 4.9 g or 88.2%. The calculated yield of ethylene glycol was 23 mmoles. The calculated number of mmoles of ethylene glycol products was 26 mmoles.

EXAMPLE XII

Example XII was conducted the same as Examples IX–XI, but here the manganese compound was added along with a solvent. A definite improvement in yield of ethylene glycol was observed.

A mixture of triruthenium dodecacarbonyl (0.213 g, 0.33 mmole), dicarbonylacetylacetonate rhodium (1) (0.258 g, 1.0 mmole), tetrabutylphosphonium bromide (5.0 g, 14.7 mmole) and methylcyclopentadienylmanganese tricarbonyl (0.055 g, 0.25 mmole) was dissolved in 5.0 g of 1-cyclohexyl-2-pyrrolidone and transferred in a glass-liner under $N_2$ purge to a 550 ml capacity pressure reactor equipped with heating and means of agitation. The reactor was sealed, flushed with $H_2/CO$ (1:1) and pressured to 204 atm. with $H_2/CO$ (1:1). The reaction mixture was heated to 220° C. with rocking, the pressure raised to 361 atm. with $H_2/CO$ (1:1) addition from the large surge tank and was maintained at 361 atm. by incremental additions from the surge tank. The reactor was held at temperature for 5 hours.

On cooling, the excess gas was vented, the dark-red liquid product (16.0 g) was recovered and analyzed.

Typical data for the distillate product on a solvent-free basis were as follows:
34.3% methanol
10.4% ethanol
1.9% ethylene glycol monomethyl ether
0.3% ethylene glycol monethyl ether
33.7% ethylene glycol
Analysis of typical gas samples showed the presence of:
47.6% hydrogen
4.6% carbon dioxide
0.5% methane
46.7% carbon monoxide The liquid yield increase was 5.5 g or 99.5% (solvent-free basis). The calculated yield of ethylene glycol was 27 mmoles. The calculated number of mmoles of ethylene glycol products was 29 mmoles.

Examples XIII and XIV demonstrate the effectiveness of having a larger mole ratio of ruthenium-to-rhodium catalyst precursor. Example XIV has a manganese component added also while Example XIII does not. The higher ruthenium-to-rhodium mole ratio leads to increase weight gains and an increase in yield of ethylene glycol products.

EXAMPLE XIII

The procedure used in Example XIII was the same as that used in Example X, except a large amount of triruthenium dodecacarbonyl (0.852 g, 1.33 mmole) and a smaller amount of dicarbonylacetylacetonate rhodium(I) (0.200 g, 0.78 mmole) were employed and tetrabutylphosphonium bromide (10.0 g, 29.4 mmole) was dissolved in 5.0 g of 1-cyclohexyl-2-pyrrolidone and was transferred in a glass-liner under $N_2$ purge to a 330 ml capacity pressure reactor equipped with heating and means of agitation. The reactor was sealed, flushed with $H_2/CO$(1:1) and pressured to 204 atm. with $H_2/CO$(1:1). The reaction mixture was heated to 220° C. with rocking. The pressure raised to 361 atm. with $H_2/CO$(1:1) addition from the large surge tank and was maintained at 361 atm by incremental additions from the surge tank. The reactor was held at temperature for 5 hours.

On cooling the excess gas was vented, the dark red liquid product (25.8 g) is recovered and analyzed. Typical data for the distillate product on a solvent-free basis are as follows:
34.7% methanol
18.6% ethanol
5.4% ethylene glycol monomethyl ether
0.4% ethylene glycol monoethyl ether
21.7% ethylene glycol
Analysis of typical gas samples showed the presence of:
46.6% hydrogen
5.3% carbon dioxide
1.5% methane
45.1% carbon monoxide The liquid yield increase was 9.7 g or 88.2% (solvent free basis). The calculated yield of ethylene glycol was 29 mmoles. The calculated number of mmoles of ethylene glycol products was 35 mmoles.

EXAMPLE XIV

A mixture of triruthenium dodecacarbonyl (0.852 g, 1.33 mmole), dicarbonylacetylacetonate rhodium (I) (0.200 g, 0.78 mmole), tetrabutylphosphonium bromide (10.0, 29.4 mmole), and methylcyclopentadienylmanganese tricarbonyl (0.218, 1.0 mmole) was dissolved in 5.0 g of 1-cyclohexyl-2-pyrrolidone and transferred in a glass-liner under $N_2$ purge to a 500 ml capacity pressure reactor equipped with heating and means of agitation. The reactor was sealed, flushed with $H_2/CO$ (1:1) and pressured to 204 atm. with $H_2/CO$ (1:1). The reaction mixture was heated to 220° C. with rocking, the pressure raised to 361 atm. with $H_2/CO$ (1:1) addition from the large surge tank and was maintained at 361 atm. by incremental additions from the surge tank. The reactor was held at temperature for 5 hours.

On cooling, the excess gas was vented, the dark-red liquid product (27.2 g) was recovered and analyzed.

Typical data for the distillate product on a solvent-free basis were as follows:
38.5% methanol
17.7 ethanol 4.6% ethylene glycol monomethyl ether
1.7% ethylene glycol monoethyl ether
19.5% ethylene glycol Analysis of typical gas samples showed the presence of:
42.9% hydrogen
6.8% carbon dioxide
22% methane
47.2% carbon monoxide The liquid yield increase was 10.9 g or 97.0% (solvent-free basis). The calculated yield of ethylene glycol was 34 mmoles. The calculated number of mmoles of ethylene glycol products was 43 mmoles.

Table I summarizes the results of Experiments I–XIV.

rhodium mole ratio is used and a cycloalkadienyl manganese tricarbonyl, said compounds being dispersed in tetrabutylphosphonium bromide and dissolved in the solvent N-cyclohexyl-2-pyrrolidone, heating said mixture to a temperature between 150° C. and 350° C. and a pressure between 70 atm and 700 atm for a sufficient time to produce the desired ethylene glycol.

2. The process as in claim 1 wherein the ruthenium-containing compound, rhodium-containing compound, manganese-containing compound, the phosphonium compound and solvent are utilized in a mole ratio of 0.1 to 4 moles of the ruthenium-containing compound, 0.1 to 4 moles of the rhodium-containing compound, 0.1 to 4 moles of the manganese-containing compound, 10 to 60 moles of the phosphonium compound and 0.1 to 60 moles of the solvent.

3. A process as in claim 1 wherein the rhodium-containing compound is dicarbonyl(acetylacetonate) rhodium.

PREPARATION OF GLYCOL AND ALKANOLS FROM SYNTHESIS GAS

| Example | Solvent (g) | Pressure (atm) | MeOH[1] | EtOH[1] | Ethylene glycol Monomethyl ether[1] | Ethylene Glycol Monoethylether[1] | Ethylene glycol[1] | mmoles of ethylene glycol | mmoles of Ethylene glycol products | Wt % of Ethylene glycol products |
|---|---|---|---|---|---|---|---|---|---|---|
| I[2] | 5.0 | 361 | 39.0 | 19.9 | 4.1 | 1.8 | 17.3 | 25 | 31 | 23.3 |
| II[2] | 10.0 | 361 | 41.3 | 18.5 | 3.8 | 1.6 | 17.8 | 24 | 29 | 23.2 |
| III[2] | 15.0 | 361 | 44.2 | 16.9 | 2.9 | 1.0 | 18.9 | 25 | 29 | 22.9 |
| IV[2] | — | 361 | 38.4 | 24.7 | 4.7 | 2.4 | 10.8 | 14 | 22 | 17.9 |
| V[2] | 5.0 | 238 | 41.5 | 24.7 | 3.1 | 1.5 | 12.7 | 8 | 10 | 17.2 |
| VI[2] | 5.0 | 306 | 39.5 | 22.4 | 4.0 | 1.8 | 15.7 | 15 | 19 | 21.4 |
| VII[2] | 5.0 | 429 | 39.6 | 20.9 | 4.9 | 2.0 | 14.8 | 27 | 36 | 21.5 |
| VIII[2] | 5.0 | 476 | 38.0 | 17.1 | 4.7 | 1.9 | 16.0 | 34 | 45 | 22.6 |
| IX[3] | — | 361 | 30.7 | 11.2 | 3.5 | 1.1 | 31.8 | 23 | 25 | 36.4 |
| X[3] | 5.0 | 361 | 34.6 | 8.9 | 1.7 | 0.3 | 37.4 | 23 | 23 | 39.4 |
| XI[4] | — | 361 | 31.4 | 12.1 | 3.6 | 1.1 | 29.2 | 23 | 26 | 33.9 |
| XII[4] | 5.0 | 361 | 34.3 | 10.4 | 1.9 | 0.3 | 33.7 | 27 | 29 | 35.9 |
| XIII[5] | — | 361 | 34.7 | 18.6 | 5.4 | 0.4 | 21.7 | 29 | 35 | 27.5 |
| XIV[6] | 5.0 | 361 | 38.5 | 17.7 | 4.6 | 1.7 | 19.5 | 34 | 43 | 25.8 |

Solvent used was N—cyclohexyl-2-pyrrolidone. Reaction conditions: $H_2/CO$ (1:1), 5 hrs. at 220° C.
[1]Values are in weight %
[2]Catalyst composition: $Ru_3CO_{12}$, 0.852 g (1.3 mmole); $Bu_4PBr$, 10.0 g (29.4 mmoles), $MeCpMn(CO)_3$, 0.218 g (1.0 mmole)
[3]Catalyst composition: $Ru_3CO_{12}$, 0.213 g (0.33 mmole); $Rh(CO)_2(C_5H_7O_2)$, 0.258 g (1.0 mmole); $Bu_4PBr$ 5.0 g (14.7 mmole)
[4]Catalyst composition: $Ru_3CO_{12}$, 0.213 g (0.33 mmole); $Rh(CO)_2(C_5H_7O_2)$, 0.258 g (1.0 mmole); $Bu_4PBr$ 5.0 g (14.7 mmole); $MeCpMn(CO)_3$, 0.055 g (0.25 mmole)
[5]Catalyst composition: $Ru_3CO_{12}$, 0.852 g (1.33 mmole); $Rh(CO)_2(C_5H_7O_2)$, 0.200 g (0.78 mmole); $Bu_4PBr$, 10.0 g (29.4 mmole)
[6]Catalyst composition: $Ru_3CO_{12}$, 0.852 g (1.33 mmole); $Ph(CO)_2(C_5H_7O_2)$, 0.200 g (0.78 mmole); $Bu_4PBr$, 10.0 g (29.4 mmole); $MeCpMn(CO)_3$, 0.218 g (1.0 mmole)

What is claimed is:

1. A process for preparing ethylene glycol in improved yield comprising:
    contacting a mixture of carbon monoxide and hydrogen in a mole ratio of 1:5 to 5:1 with a catalyst system comprising
    triruthenium-dodecacarbonyl combined with a rhodium-carbonyl wherein a higher ruthenium-to-